United States Patent [19]

Moore

[11] Patent Number: Plant 5,686

[45] Date of Patent: Mar. 11, 1986

[54] BLACKBERRY-SHAWNEE CULTIVAR

[75] Inventor: James N. Moore, Fayetteville, Ark.

[73] Assignee: University of Arkansas Agricultural Experiment Station, Fayetteville, Ark.

[21] Appl. No.: 628,143

[22] Filed: Jul. 5, 1984

[51] Int. Cl.[4] ..... A01H 5/00

[52] U.S. Cl. ..... Plt./46

[58] Field of Search ..... Plt./46

*Primary Examiner*—James R. Feyrer

[57] ABSTRACT

Description and specifications of a new and distinct blackberry variety which originated from seed produced by a hand-pollinated cross of Cherokee (non-patented) and Arkansas Selection 586 (non-patented) is provided. This new blackberry variety can be distinguished by its late fruit ripening, large fruit size, high fruit productivity, and very erect cane growth habit.

2 Drawing Figures

SUMMARY OF THE INVENTION

The new and distinct variety of blackberry originated from a hand-pollinated cross of Cherokee (non-patented) × Arkansas Selection 586 (non-patented) made in 1971 at the Arkansas Agricultural Experiment Station Fruit Substation at Clarksville, Ark. The seeds resulting from this controlled hybridization were germinated in a greenhouse in the spring of 1972 and planted in a field on the Arkansas Agricultural Experiment Station at Clarksville, Ark. The seedlings fruited during the summer of 1974 and one, designated Ark. 730, was selected for its large fruit size, erect growth habit, and high productivity.

During 1975, the original plant selection was propagated asexually from root cuttings and a test row of 20 plants was established. Subsequently, larger test plantings have been established with asexually multiplied plants at six additional locations in Arkansas and on state and/or federal experiment stations in New York, Louisiana, Maryland, Texas, North Carolina and Alabama.

The new variety has been asexually multiplied annually since 1975 by the use of root cuttings and by rooting softwood cuttings. It forms new plants from adventitious buds on root cuttings readily and also roots well from softwood cuttings. During all asexual multiplication, the characteristics of the original plant have been maintained and no aberrant phenotypes have appeared.

Test plantings over a wide geographic area have shown this new variety to be adapted to differing soil and climatic conditions. It has performed well in tests in the Southeast U.S. but is not coldhardy in northern states.

Plants of the new variety are highly vigorous and prolific and row establishment following planting is rapid. Both primocanes and floricanes are very erect and the fruit is readily accessible to both machine and hand harvest. Thorn size and density are medium, similar to Cherokee and Cheyenne varieties. Plants and fruit are moderately tolerant to anthracnose (*Elsinoe veneta* (Burkh.) Jenkins), and plants are immune to orange rust (*Gymnoconia peckiana* (Howe) Trott).

Fruit of the new variety ripens late, about 5 days after the Cheyenne variety. Average ripening date is June 18 in central Arkansas. The harvest period is longer than most other erect varieties; it produces well for a full month. This long fruiting period results in high total yields and the new variety has consistently outyielded the standard varieties Cherokee, Comanche and Cheyenne.

The fruit is long conic in shape, bright black in color and very large in size (ca. 7.7 g). Fruit size is maintained well throughout the season, without the significant decline in size of secondary and tertiary fruits common in other varieties. The fruit is firm at maturity, being equal to that of the Cheyenne variety and better than that of the Comanche variety.

The fresh fruit has better flavor than the Comanche variety, is equal to Cheyenne, and slightly less flavored than Cherokee. Fruit processed by canning is of good quality, equal to Cherokee and Cheyenne, and superior to Comanche. Seed size is slightly larger than Cherokee but smaller than the Comanche variety.

Fruit clusters are medium-large, cymose, and are borne on the periphery of the plant canopy, providing easy access to harvest. Flower fertility is high and clusters are well filled.

The new variety has been named the Shawnee cultivar.

BRIEF DESCRIPTION OF THE PHOTOGRAPHS

The accompanying photographs show typical specimens of the fruit and leaf of the new variety in color as nearly true as it is reasonably possible to make in a color illustration of this character.

DETAILED DESCRIPTION OF THE NEW VARIETY

The following is a detailed description of the pomological characteristics of the subject blackberry. Color terminology is in accordance with that of The Royal Horticultural Society Colour Chart published in 1966 by The Royal Horticultural Society of London, England.

Where dimensions, sizes, colors and other characteristics are given, it is to be understood that such characteristics are approximations of averages set forth as accurately as practicable.

The descriptions reported herein are from specimens grown at Clarksville, Ark. unless otherwise noted.

Plant:

*Size.*—Large, very erect.

*Growth.*—Very vigorous; prolific suckering from roots and crowns.

*Productivity.*—Very high and for duration of one month; consistent from year to year.

*Cold hardiness.*—Medium, similar to Cheyenne.

*Canes.*—Very erect. Cane diameter: base 15.6 mm, midpoint 12.0 mm, terminal 6.9 mm. Internode length: base 22.4 mm, midpoint 50.0 mm, terminal 25.4 mm. Thorn density (per 30 cm): base 30.0, midpoint 37.0, terminal 42.0. Floricane color: base Brown Group (200D), midpoint Brown Group (200C), terminal Brown Group (200B). Primocane color: base Yellow-Green Group (146B), terminal Yellow-Green Group (146B).

*Disease resistance.*—Moderate for anthracnose; immune to orange rust.

Foliage:

*Leaves.*—Large. Color: Floricane base Yellow-Green Group (147A), floricane terminal Yellow-Green Group (147A); Primocane base Yellow-Green Group (147A), primocane terminal Yellow-Green Group (146A).

Flowers:

*Date of first bloom.*—Apr. 16.

*Date of last bloom.*—May 3.

*Blossom color.*—Yellow-White Group 158D with slight pink at border.

*Reproductive organs.*—Stamens — Erect, numerous. Pistils — Numerous. Pollen — Normal and abundant.

Fruit:

*Maturity.*—Late, 5 days after Cheyenne. Average ripe date June 18. Average period of maturity June 18–July 19.

*Size.*—Large, average 7.7 g, uniform.

*Shape.*—Medium long conic, uniform.

*Color.*—Glossy black.

*Skin.*—Medium tender.

*Drupelet size.*—Medium.

*Seed size.*—Medium large.

*Firmness.*—Good, equal to Cheyenne.

*Flavor.* —Good, mildly acid.

*Soluble solids.*—9.9%.

*pH.*—3.04.

*Total acids.*—1.293%.

*Processed quality.*—Good, equal to Cheyenne.

*Uses.*—Fresh and processed, jellies, jams.

The variety:

The most distinctive features of the variety are its large fruits, high productivity, late ripening and very erect cane growth habit.

I claim:

1. A new and distinct variety of blackberry, substantially as illustrated and described, characterized by its late ripening, large fruits, high productivity and very erect cane growth habit.

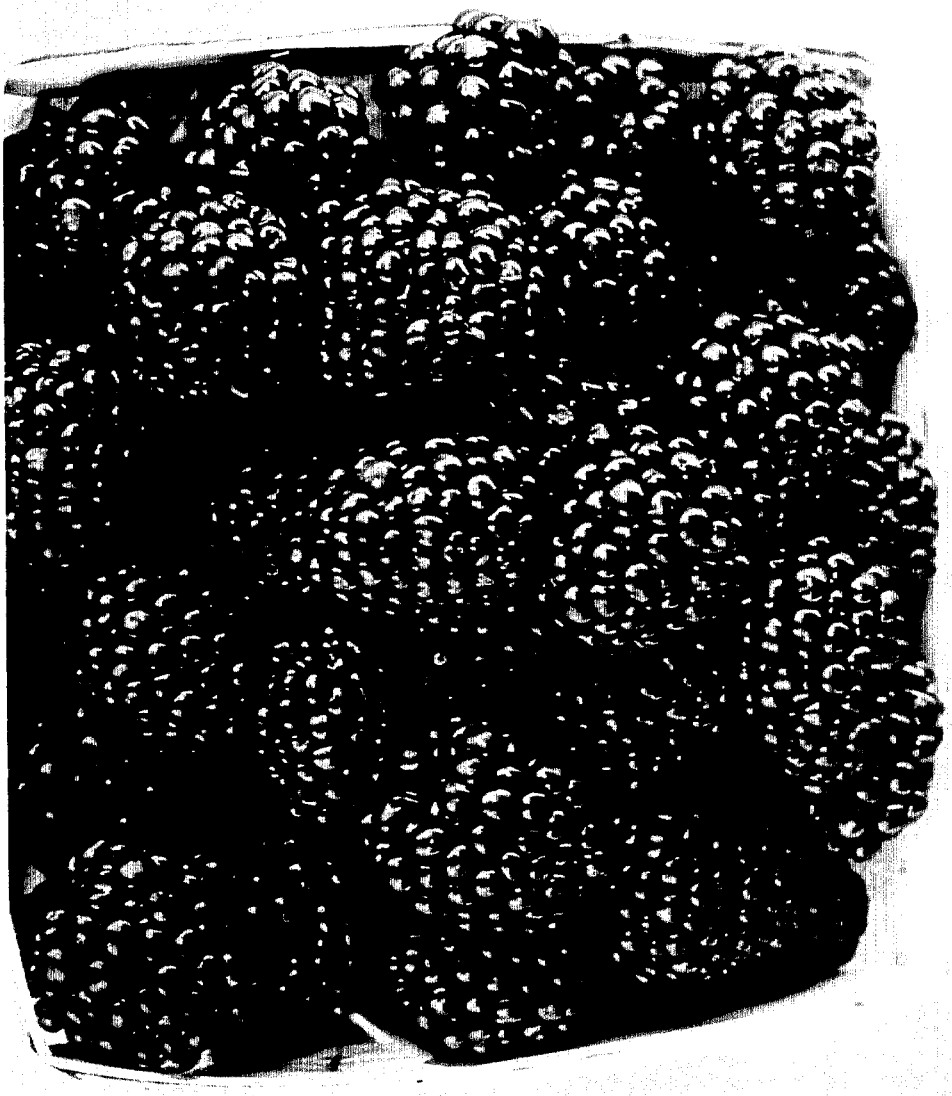

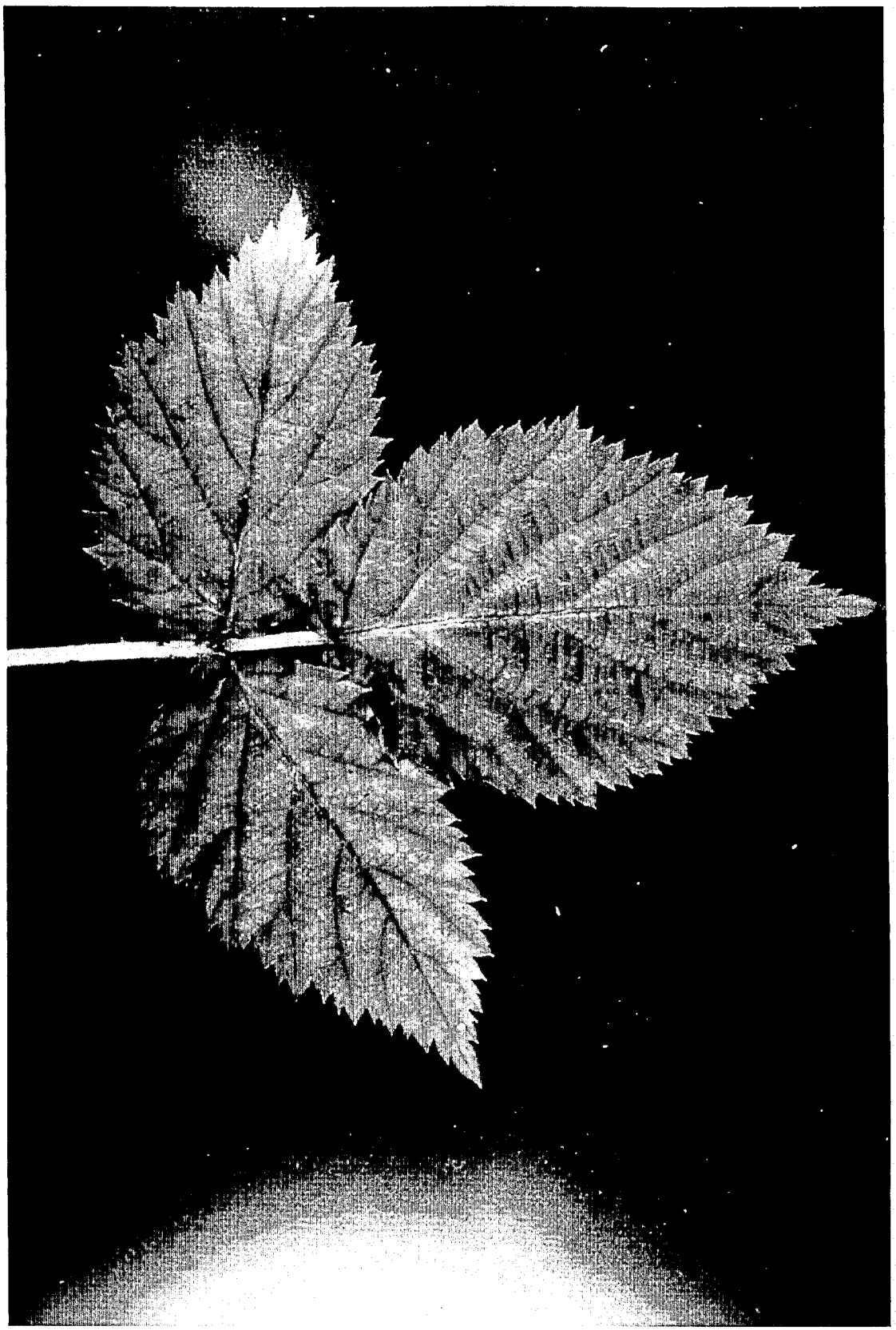

* * * * *